United States Patent [19]
> Wideman

[11] Patent Number: 4,762,962

[45] Date of Patent: Aug. 9, 1988

[54] PROCESS FOR THE ISOMERIZATION OF BRANCHED DIENES

[75] Inventor: Lawson G. Wideman, Tallmadge, Ohio

[73] Assignee: The Goodyear Tire & Rubber Company, Akron, Ohio

[21] Appl. No.: 59,370

[22] Filed: Jun. 8, 1987

[51] Int. Cl.$^4$ .................. C07C 5/27; C07C 11/12
[52] U.S. Cl. ..................... 585/671; 585/601; 585/667
[58] Field of Search .............. 585/667, 671, 601

[56] References Cited

U.S. PATENT DOCUMENTS 2,281,804  5/1942  Ruthruff .................. 585/671
2,404,340  7/1946  Zimmerman ............. 585/671
2,554,202  9/1948  McNeil et al. ............ 585/671

FOREIGN PATENT DOCUMENTS 977233  5/1962  United Kingdom ........ 585/601

*Primary Examiner*—Patrick P. Garvin
*Assistant Examiner*—George R. Fourson
*Attorney, Agent, or Firm*—D. O. Nickey

[57] ABSTRACT

This invention relates to a process for the isomerization of branched dienes which comprises contacting at isomerization conditions a branched diene with a boron phosphate catalyst wherein the initial ratio of phosphorus (P) to boron (B) is less than 1.0 but greater than 0.6. The contacting is conducted at a temperature of from 100° C. to 450° C. and at a pressure from subatmospheric to superatmospheric.

14 Claims, No Drawings

PROCESS FOR THE ISOMERIZATION OF BRANCHED DIENES

TECHNICAL FIELD

This invention relates to a process for the isomerization of branched dienes. More specifically, this invention is concerned with a catalyst for the conversion of 2-ethyl-1,3-butadiene to 3-methyl-1,3-pentadiene and the conversion of 3-methyl-1,3-pentadiene to 2-ethyl-1,3-butadiene.

BACKGROUND ART

Dienes, especially isoprene, are useful as monomers for the manufacture of synthetic rubbers. Several fundamental processes have been used to construct the isoprene $C_5$ skeleton from smaller carbon units. These processes are not commercially accepted in that there are numerous problems associated with each particular synthesis route.

One avenue to the construction of a $C_5$ skeleton uses linear butenes which are catalytically isomerized to a mixture of cis- and trans-butene-2 and then hydroformylated to produce 2-methylbutanal (2MBA) in the presence of a homogeneous rhodium catalyst and an organic ligand. The 2MBA is then dehydrated to isoprene in the presence of acidic heterogeneous catalysts at elevated temperatures. U.S. Pat. No. 4,524,233 discloses and claims a process for the conversion of an aldehyde to a diolefin comprising contacting an aldehyde of 4 to 6 carbon atoms in the vapor phase at a temperature of from 200° to 400° C. with a boron phosphate catalyst wherein the initial molar ratio of phosphorus to boron is less than 1 but greater than 0.6 which is in intimate admixture with from 0.1 to 10 weight percent graphite. This patent discloses the dehydration of aldehydes such as 2-methylbutanal, 2,3-dimethylbutanal and 2- or 3-ethylbutanal. The dienes that are produced as a result of this process include 1,3-butadiene, isoprene, 1,3-hexadiene, 2, 3, or 4-methyl-1,3-pentadiene, 2,3-methylbutadiene and 2-ethyl-1,3-butadiene.

Those knowledgeable in the art of polymer synthesis are constantly searching for new monomers which may be useful in the preparation of polymers that possess unique physical properties. Two monomers of particular interest are 3-methyl-1,3-pentadiene and 2-ethyl-1,3-butadiene. These monomers can be prepared from the dehydration of 2-ethylbutanal. In the dehydration of 2-ethylbutanal, the major dehydration products produced are ethyl butadiene and 3-methyl-1,3-pentadiene with the production of 3-methyl-1,3-pentadiene being predominate. It would be especially useful to have a process which would allow for the conversion of 2-ethyl-1,3-butadiene to 3-methyl-1,3-pentadiene or vice versa.

An article by Higashimura and Hasegawa, Journal of Polymer Science, Vol. 17, 2439–2446 (1979) entitled, "Monomer-Isomerization Oligomerization of 2-Ethyl-1,3-Butadiene by Acid Catalysts" discloses the cationic oligomerization of 2-ethyl-1,3-butadiene (2EBD) by a superacid which is accompanied by monomer isomerization to 3-methyl-1,3-pentadiene (3MPD) before propagation to yield oligomers of the isomerized monomer as the main product in benzene at 50° C. This article deals with the oligomerization of 2-ethyl-1,3-butadiene which is easier to handle at high temperatures than volatile butadiene and isoprene. The authors found that a superacid catalyzed oligomerization of 2EBD initially isomerizes to 3-methyl-1,3-pentadiene before propagation and yields primarily 3MPD oligomers. This article does not suggest or disclose the instant discovery that a specific boron phosphate catalyst will allow for the conversion of these branched dienes without oligomerization or polymerization of the desired monomeric material.

U.S. Pat. No. 3,607,968 is concerned with the isomerization of aliphatic olefins having 9 to 22 carbon atoms in the presence of a boron phosphate catalyst at elevated temperatures. This patent does not suggest or disclose the use of a specific boron phosphate catalyst under specific conditions to achieve the desired isomerization of a branched diene.

U.S. Pat. No. 4,537,995 is concerned with a process for isomerizing branched aldehydes to ketones which comprises contacting at isomerization conditions a branched aldehyde with a zeolite catalyst. The crystalline aluminosilicate zeolites used in this patent are referred to generally as ZSM-5 type or behaving like ZSM-5 type zeolites. The process is typically conducted in the vapor phase utilizing temperatures as low as 325° C.

U.S. Pat. No. 4,632,913 is concerned with an improved boron phosphate dehydration catalyst wherein the boron phosphate has been treated with an ammonium carbonate or bicarbonate salt prior to calcination.

U.S. Pat. No. 4,628,140 is directed to an improved process for the conversion of an aldehyde to a diolefin comprising contacting an aldehyde of 4 to 6 carbon atoms in the vapor phase with a catalyst, the improvement comprising the addition of from 0.10 to 5 percent by weight of an aromatic compound to the aldehyde feed.

The use of acid catalysts to perform isomerization reactions is known and boron phosphate is known to catalyze certain isomerization reactions: however, there is no suggestion or disclosure from the prior art that a specific boron phosphate catalyst wherein the P/B ratio is less than 1 would allow for the conversion of 3-ethyl-1,3-butadiene to 3-methyl-1,3-pentadiene and vice versa with exceptional conversions and high selectivities without the attendant problems of catalysts fouling, reduced catalyst lifetimes or diene oligomer formation.

A disadvantage associated with known catalysts to isomerize unsaturated materials is that catalyst life depends on many factors which includes catalyst composition, structure, catalyst activity, operating temperatures and coke deposition. Coke deposition is understood to denote coke (carbonaceous) deposits formed on the catalyst during the isomerization reaction. The use of boron phosphate as a catalyst for the isomerization of monoolefins and aldehydes is known: however, the problems associated with a diene isomerization are different and more difficult to overcome than those found in monoolefin or aldehyde isomerizations. The isomerization of a diolefin such as 2EBD or 3MPD is difficult since these highly reactive monomers are known to form dimers and/or polymerize in the presence of acid catalysts. Due to these and other differences, catalysts suitable for long term isomerization of dienes have not found acceptance in the preparation of these desirable monomeric materials.

One aspect of this invention is directed to the use of graphite which is an intimate physical admixture with the boron phosphate. Graphite has numerous known uses including utility as carrier for catalysts and as a lubricant during catalyst pellet formation. See U.S. Pat. No. 1,841,055. The prior art does not suggest, disclose or appreciate that the presence of graphite in a boron phosphate catalyst will unexpectedly enhance the viable lifetime of the catalyst in a diene isomerization reaction.

A portion of the instant invention is directed to a catalyst of high selectivity and low coke deposition in conjunction with extended catalyst life times. The prior art does not suggest or disclose a specific catalyst or process for the isomerization of dienes which would be suitable for commercial application.

Disclosure of the Invention

There is disclosed a process for the isomerization of a branched diene which comprises passing the branched diene in the vapor phase over a boron phosphate catalyst, the improvement comprising a catalyst which has an initial molar ratio of P/B of less than 1.0 but more than 0.6.

There is disclosed a process for the conversion of 2-ethyl-1,3-butadiene to 3-methyl-1,3-pentadiene which comprises contacting the 2-ethyl-1,3-butadiene in the vapor phase at a temperature of from 100° to 200° C. with a boron phosphate catalyst, said catalyst is characterized in that the initial molar ratio of phosphorus (P) to boron (B) (P/B) is less than 1.0 but greater than 0.6.

There is also disclosed a process for the conversion of 2-ethyl-1,3-butadiene to 3-methyl-1,3-pentadiene as described above wherein the boron phosphate catalyst is in physical admixture with from 0.1 to 10 weight percent graphite.

There is further disclosed a process for the conversion of 3-methyl-1,3-pentadiene to 2-ethyl-1,3-butadiene which comprises contacting the 3-methyl-1,3-pentadiene in the vapor phase at a temperature from 250° to 450° C. with a boron phosphate catalyst, said catalyst is characterized in that the initial molar ratio of phosphorus (P) to boron (B) (P/B) is less than 1.0 but greater than 0.6.

There is also disclosed a process for the conversion of 3-methyl-1,3-pentadiene to 2-ethyl-1,3-butadiene as described above wherein the boron phosphate catalyst is in physical admixture with from 0.1 to 10 weight percent graphite.

In addition, there is disclosed a process for the conversion of 3-methyl-1,3-pentadiene to 2-ethyl-1,3-butadiene which comprises contacting the pentadiene in the vapor phase at a temperature from 250° to 450° C. at a LHSV of 1.0 to 20 with a boron phosphate catalyst, the improvement characterized in that the boron phosphate catalyst is prepared by (1) combining phosphoric acid and boric acid and/or trialkyl borate wherein the alkyl group is from 1 to 6 carbon atoms; (2) at such molar ratios that the molar ratio of P/B is less than 1 but greater than 0.6: (3) admixing the boron phosphate with from 0.1 to 10 weight percent graphite based on total weight of the boron phosphate: (4) calcining the boron phosphate in air at a temperature from 250° C. to 650° C. for 1 to 6 hours and: (5) steaming the calcined boron phosphate at 200° to 300° C. for ½ to 10 hours. In like fashion, 2-ethyl-1,3-butadiene can be converted to 3-methyl-1,3-pentadiene over the same catalyst but at a temperature of from 100°-200° C.

A portion of this invention relates to the discovery that branched dienes with conjugated double bonds can be isomerized with commercial and economic advantage by contacting the diene with a boron phosphate catalyst wherein the ratio of P/B is less than 1, preferably less than 0.9 but greater than 0.6.

Examples of the branched dienes which are suitable for use in the process according to this invention include 2-ethyl-1,3-butadiene: 3-methyl-1,3-pentadiene: 2-methyl-1,3-pentadiene: 4-methyl-1,3-pentadiene: and the like.

The process according to the invention is generally carried out at temperatures from 100° to 200° C. when converting the butadiene to the pentadiene and from 250° to 425° C. when converting the pentadiene to the butadiene.

Representative of the solvents which are useful in the isomerization reaction include pentane, hexane, heptane, octane, nonane and other hydrocarbons which are miscible with the branched diolefin and will not interfere with the isomerization reaction.

Isomerization of the branched diolefin by the process according to this invention can be carried out at ambient pressure: for example, by vaporizing the diolefin and passing it over the catalyst with or without a carrier gas. Inert gases such as nitrogen, carbon dioxide or hydrocarbons, especially saturated hydrocarbons, have proved to be particularly advantageous carrier gases.

The instant invention can also be carried out under reduced pressure. In which case a reduced pressure of from 0.60 to 1.33 Pa below atmospheric pressure has been found acceptable. Compression pressures of from 2 to 10 bar, more particularly from 2 to 4 bar, can be regarded as both suitable and adequate. The isomerization catalysts, according to this invention, are boron phosphates wherein the initial molar ratio of P/B can range from 0.6 to 1.0 which may or may not be in physical admixture with from 1 to 10 weight percent graphite. Initial molar ratio means that the catalyst charged to the reaction or pretreatment vessel has a P/B ratio of less than 1. It has been discovered that during the use or steam pretreatment of these catalysts, the ratio of P/B approaches but never exceeds 1.0. It has also been found that the catalyst of the invention can be advantageously pretreated with steam. For example, a catalyst with an initial P/B ratio of 0.8 is placed in the reactor or suitable vessel and ambient pressure steam is passed over the catalyst at an LHSV of at least 2.0, preferably 2.25 for at least a ½ hour. By an LHSV of 2.25 is meant 2.25 volumes of liquid water per volume of catalyst is passed through the preheater for vaporization and then over the catalyst. It will be demonstrated later that this catalyst after use or pretreatment is substantially different than a catalyst with an initial ratio of 1.0 or greater.

Useful isomerization catalysts can be synthesized using known techniques such as reacting phosphoric with a trialkyl borate. These high surface area boron phosphate isomerization catalysts have surface areas based upon nitrogen absorption of up to 220 m² per gram.

The catalyst of the instant invention can also be synthesized via the paste method. In the paste method, the amount of reagent grade 85% phosphoric acid required to give the desired mole ratio is placed in a glass reactor, heated to 70° C. and powdered grade orthoboric acid is added slowly with stirring. After the 6 hours, the heat is removed and the resultant paste is spread over the inner surface of a glass tube and is heated to 110° C. in air for 16 hours. The white solid is chipped from the tube and stored in tightly sealed glass bottles. Prior to use the sample is ground and sieved through a 20–30 mesh sieve.

The catalyst can be used both in piece form (pelletized) for example in a fixed bed reactor and also in a fluidized bed reactor and in the form as prepared or even applied to an inert supporting material.

The dimensions of the catalyst are governed by the type of reactor used. In cases where a tube reactor is used as a fixed bed reactor, a tube diameter of from 10 to 15 millimeters has proved to be advantageous. The reactor is thus packed with catalyst particles in the form of granules, cylinders, pellets or spheres with an average diameter of the individual particles of from 2 to 12 millimeters, more particularly from 4 to 8 millimeters. In the case of a fluidized bed reactor, the catalysts used for the process are in the form of catalyst particles with dimensions of from 20 to 200 microns, preferably from 40 to 80 microns.

Continuous fluidized beds and batch reactors can be used with equal effect for the process according to the invention. Only the working up of the reaction products will determine the particular method adopted. The fixed bed reactor is preferably used in the instant process with or without the use of a carrier gas.

The graphite utilized in the present invention is characterized by a surface area of about 1 to 1000 m² per gram. Suitable graphites useful in the instant invention include both the natural and synthetic varieties which are produced by heating petroleum coke to 3000° C. in an electric furnace. Graphite is added to the boron phosphate during the mixing of the phosphoric acid with the boric acid/alkyl borate or after the resulting material has been dried and sieved. It is preferred to combine the graphite with the boron phosphate after the paste has been dried and sieved but before the catalyst is pressed or extruded in the form of rods or pellets.

During the isomerization reaction it has been found to be advantageous to recycle the unconverted materials back to the reactor. This may be accomplished in the same reaction zone or in a second reaction zone so that there is no loss of selectivity.

Dilution of the feed to the isomerization reactor with a hydrocarbon such as heptane may be advantageous. Dilution of the feed at ratios of from 0 to 80% by weight with an inert hydrocarbon is suitable. One skilled in the art will appreciate that any solvent for the branched diolefin which does not interfere with or enter into the isomerization reaction would be appropriate.

An advantage of the process of the instant invention is that the mild reaction conditions enable both the starting material and the reaction product to be sparingly treated and this is reflected in the high selectivity of the reaction. The instant invention has proved to be advantageous in that lesser amounts of tar or coke are formed during the isomerization reaction. In the presence of catalysts previously used for isomerization reactions. tar formation occurs to such an extent that after reacting for 30 to 60 minutes, there is a substantial decrease in both activity and selectivity of the catalyst. In order to regenerate such coke catalysts, the deposits would have to be burnt off and after several regenerations, the catalysts may be totally useless.

BEST MODE FOR CARRYING OUT THE INVENTION

Catalyst Preparation

High surface area boron phosphate catalysts were prepared by adding phosphoric acid (for example, 88.34 grams of 85% acid) to a 500 ml resin kettle. The resin kettle was equipped with paddle stirrer, oil bath, thermometer and nitrogen/inlet exit. A trialkyl borate such as tripropyl borate (210.03 ml) was syringed into an addition funnel. After the resin kettle was purged with nitrogen, the trialkyl borate was slowly added to the stirred phosphoric acid at room temperature. No exotherm was noted. After the addition was complete, the oil bath was quickly heated to 120° C. and maintained at a temperature between 120° and 130° C. The nitrogen flow was increased and glass stoppers were removed to flush the resulting alcohol from the trialkyl borate from the reaction mixture. After about 7 minutes, the reaction mixture had thickened to a jellylike consistency. The reaction temperature was maintained at about 130° C. until the mixture could only be stirred with difficulty. The thick jell was then transferred to a 500 ml beaker and dried in a 65° C. vacuum oven overnight. The next day the finished catalyst was screened to a mesh of 35. The same procedure was used to prepare numerous catalysts of varying P/B molar ratios.

Using the paste method, a glass reactor fitted with a stirrer, a condenser and a heating mantle was charged with various amounts of boric acid and/or trialkyl borate and phosphoric acid to achieve the desired P/B molar ratios. The acids were heated to 70° C. and stirred for 6 hours. The paste was removed and spread over the inner surface of the glass tube and heated to 110° C. in air for 16 hours. The white solid was chipped from the tube and sieved. The same procedure was used to prepare numerous catalysts of varying P/B ratios. Portions of these catalysts were combined with graphite in the appropriate amounts and then extruded into rod forms or pressed into pellets.

The boron phosphates prepared as described above may be calcined or steam treated prior to use in the isomerization reaction or they may be used as is after drying. Steam treatment can be conducted in a separate vessel or in the reactor. When using the reactor, water is feed to the preheater of a rate of 1.5 to 2.5 volumes of liquid water per volume of catalyst per hour and thereafter passed over the catalyst at ambient pressure for at least ½ hour and up to 6 hours. This steam treatment produces a catalyst with a P/B ratio that approaches but does not exceed 1.0. It has been discovered that steaming a catalyst with a P/B ratio of 0.8, for example, leeches the excess boric acid and produces a catalyst that is superior to a catalyst with an initial P/B ratio of 1.0 or greater.

Reactor System

The data for the following examples were obtained from a reactor system which consists of a 1.25 cm by 30 cm Pyrex TM tube and a pump system for delivery of the branched diene. The reactor also contained a 6 cm×2 cm preheater filled with Pyrex TM beads. Three thermocouples were situated in the reactor—one in the preheater section; one in the first half of the catalyst bed: and one in the lower half of the catalyst bed. The reactor was enclosed with fiberglass heating tapes and wrapped additionally with fiberglass tape. Temperature controls were used on the three separate heaters so that each portion was independently heated and controlled. The reactor was thus run under isothermal conditions.

The pump was used to charge the branched diolefin feed continuously into the reactor in a down flow manner with a cocurrent nitrogen flow of about 14 ml per minute. The effluent from the reactor was passed into a dry ice trap which served as the container for the reaction product. The reactor was run at atmospheric pressure. The nitrogen gas was used as a protective blanket for the catalyst feed and effluent system. The nitrogen may also serve as a mild diluent and carrier gas: although, a nitrogen flow as low as 7 ml per minute changed very little in the reaction system.

The liquid hourly space velocity (LHSV) of the branched diolefin entering the preheater was set at 2.25 for all reactions. However, the LHSV can be varied and can be defined by more than one set of conditions. Therefore, as used herein LHSV is the volume of liquid feed per hour that is passed over the total volume of catalyst. Total volume of catalyst is obtained by pouring the catalyst into a graduated cylinder to a mark, for example 40 cc. The LHSV is calculated by dividing the volume of catalyst into the volume of liquid feed per hour. The effluent from the reactor was analyzed with a gas chromatograph having a 70 m column packed with a suitable material for resolving the components in the reaction mixture. Suitable packing materials, such as TCEP on chromosorb P are known to those skilled in analytical chemistry. Other conditions of the gas chromatograph were: (1) detector temperature—210° C. (2) injection port temperature—210° C.: (3) oven temperature program of 3 minutes at 70° C. followed by a 7.5° C. per minute rise to 130° C. Standards were prepared and the response factors were determined for the ethylbutadiene and the pentadiene with nonane as the weighed internal standard.

An additional aspect of this invention resides in the ability to increase the yield of 3-methyl-1,3-pentadiene from the dehydration of 2-ethylbutanal by converting the ethylbutadiene into 3-methyl-1,3-pentadiene. As discussed previously, the dehydration of 2-ethylbutanal over an acid catalyst gives ethylbutadiene and 3-methyl-1,3-pentadiene as the major products. The ethylbutadiene and the 3-methyl-1,3-pentadiene are easily separated by distillation. The ethylbutadiene is then passed in the vapor phase over the catalyst to unexpectedly isomerize in high selectivity to the 3-methyl-1,3-pentadiene and vice versa.

The following examples are submitted to illustrate the present invention and are not intended to limit the same.

EXAMPLE 1

2-Ethyl-1,3-butadiene (EBD) was passed over a 0.8 P/B catalyst that contained 1% graphite by weight which was steam treated prior to use. The temperature of the reaction was 150° C. and after 1 hour on stream at a LHSV of 2.25, the conversion of ethylbutadiene was 86% and the selectivity to 3-methyl-1,3-pentadiene was 85%.

EXAMPLE 2

A reaction was carried out under the conditions of Example 1, except the reactor temperature was 200° C. The ethylbutadiene conversion was 76.9% and the 3-methyl-1,3-pentadiene selectivity was 93.1%.

EXAMPLE 3

Control

A reaction was carried out under the conditions of Example 1, except the reactor temperature was 250° C. The ethylbutadiene conversion was 88.8% and the 3-methyl-1,3-pentadiene selectivity was 36%. Appreciable oligomer formation was noted.

EXAMPLE 4

Control

A reaction was carried out under the conditions of Example 1, except the reactor temperature was 300° C. The ethylbutadiene conversion was 90.4% and the 3-methyl-1,3-pentadiene selectivity was 63.5%. This example and Example 3 demonstrate that temperatures above 200° C. are detrimental to the selectivity of the reaction to produce the desired product and promotes the formation of oligomers which results in coking of the catalyst.

EXAMPLE 5

Control

A reaction was carried out under the conditions of Example 1, except the catalyst was a 5 Å molecular sieve. The EBD conversion was 10.7% and the 3-methyl-1,3-pentadiene selectivity was 96.2%.

EXAMPLE 6

Control

A reaction was carried out under the conditions of Example 5, except the reactor temperature was 200° C. The ethylbutadiene conversion was 56.5% and the 3-methyl-1,3-pentadiene selectivity was 97%.

EXAMPLE 7

Control

A reaction was carried out under the conditions of Example 5, except the reactor temperature was 250° C. The ethylbutadiene conversion was 85% and the 3-methyl-1,3-pentadiene selectivity was 40%. In Examples 5, 6 and 7, it was noted that coke formation on the catalyst was observed after only one hour on stream. It is believed that these catalysts would be plugged or deactivated within a very short period of time. In addition, Examples 5–7 demonstrate that known molecular sieves are inferior to the catalyst of this invention for the isomerization of a branched diene.

As discussed previously, the yield of 2-ethyl-1,3-butadiene from the dehydration of 2-ethylbutanal can be greatly increased by converting the unwanted 3-methyl-1,3-pentadiene into 2-ethyl-1,3-butadiene. The dehydration of 2-ethylbutanal over an acid catalyst gives 3-methyl-1,3-pentadiene cis- and trans- as the major product with concurrent formation of EBD. The ethylbutadiene is readily distilled from the reactor effluent (boiling point of 66° C.), then 3-methyl-1,3-pentadiene is distilled from the effluent (boiling point 77° C.). The distilled 3-methyl-1,3-pentadiene was then passed over a catalyst according to this invention at 275° to 400° C. to form ethylbutadiene in 7 to 10% yield with high selectivity. The newly synthesized ethylbutadiene is distilled from the reactor effluent and the unreacted 3-methyl-1,3-pentadiene is recycled back to the isomerization reactor. Make up 3-methyl-1,3-pentadiene was added as required.

EXAMPLE 8

3-methyl-1,3-pentadiene was passed over a 0.8 P/B catalyst with 1% graphite by weight at 275° C. After 1 hour on stream at an LHSV of 2.25, the reactor effluent consisted of 7% ethylbutadiene and 92% 3-methyl-1,3-pentadiene.

EXAMPLE 9

A reaction was carried out under the conditions of Example 8 except 3-methyl-1,3-pentadiene was passed over the catalyst at 350° C. for 1 hour. The reactor effluent consisted of 9% ethylbutadiene and 90% 3-methyl-1,3-pentadiene.

EXAMPLE 10

3-methyl-1,3-pentadiene was passed over a 0.8 P/B catalyst with 1% graphite by weight at 400° C. for 1 hour at an LHSV of 2.25. The reactor effluent consisted of 10.1% ethylbutadiene and 86% 3-methyl-1,3-pentadiene. Examples 8–10 demonstrate that the catalyst of this invention is highly selective in converting the methylpentadiene to the ethylbutadiene.

EXAMPLE 11

Control 3-methyl-1,3-pentadiene was passed over a Mordenite (silicon oxide/aluminum oxide at a 10:1 ratio) catalyst in the acid form at 275° C. for 1 hour at an LHSV of 6.0. The reactor effluent consisted of 6.4% ethylbutadiene, 79% 3-methyl-1,3-pentadiene with the balance being lights and oligomers.

EXAMPLE 12

Control

A run was carried out under the conditions of Example 11, except the reactor temperature was 350° C. The reactor effluent consisted of 10.2% ethylbutadiene and 76% 3-methyl-1,3-pentadiene with the balance being lights and oligomers.

EXAMPLE 13

Control

A run was carried out under the conditions of Example 11, except the reactor temperature was 400° C. The reactor effluent consisted of 11.4% ethylbutadiene and 74% 3-methyl-1,3-pentadiene with the balance being lights and oligomers. Examples 11–13 demonstrate that the known isomerization catalyst, Mordenite, is inferior to the catalyst of this invention for the isomerization of branched dienes.

EXAMPLE 14

Control

A run was also carried out under the conditions of Example 1, except the catalyst was solid phosphoric acid on Kieselguhr 3/16" spheres. The reactor effluent consisted of mostly oligomers and a trace of methylpentadienes and ethylbutadienes.

EXAMPLE 15

A run was carried out under the conditions of Example 10, except the catalyst was a 0.8 P/B without graphite. The reactor effluent consisted of 8.1% ethylbutadiene and 70% 3-methyl-1,3-pentadiene plus oligomers.

EXAMPLE 16

Control WL

A run was conducted under the conditions of Example 1, except the LHSV was 0.6. The reactor effluent consisted of 4.9% ethylbutadiene by weight and 60% 3-methyl-1,3-pentadiene by weight, plus several unidentified by-products.

EXAMPLE 17

A run was carried out under the conditions of Example 1, except that the LHSV was 20. The reactor effluent consisted of 4.1% ethylbutadiene by weight and 5.4% 3-methyl-1,3-pentadiene by weight.

Example 18

CONTROL

A run was carried out under the conditions of Example 1 except the catalyst was 1.1 P/B without graphite. The EBD conversion was 99% and the selectivity to 3-methyl-1,3-pentadiene was 0.5%. Mostly oligomers were detected. This example evidences the criticality that the catalyst has a P/B ratio of less than 1.0 to be effective.

EXAMPLE 19

Control

A run was carried out under the conditions of Example 18 except the reaction temperature was 275° C. The EBD conversion was 99% and the selectivity to 3-methyl-1,3-pentadiene was 1.5%. Mostly oligomers were detected.

EXAMPLE 20

Control

A run was carried out under the conditions of Example 8 except the catalyst was 1.1 P/B with 1% graphite by weight. The 3-methyl-1,3-pentadiene conversion was 98% and the selectivity to EBD was 0.3%. Mostly oligomers were detected.

EXAMPLE 21

Control

A run was carried out under the conditions of Example 20 except the reaction temperature was 350° C. The 3-methyl-1,3-pentadiene conversion was 99% and the EBD selectivity was 0.2%. Mostly oligomers were detected.

EXAMPLE 22

Control

A run was carried out under the conditions of Example 1 except the catalyst was 1.0 P/B with 1% graphite. The EBD conversion was 80% and the 3-methyl-1,3-pentadiene was 14%. Mostly oligomers were detected. This control demonstrates that the use of graphite is not beneficial unless the P/B ratio is less than 1.0.

EXAMPLE 23

Control

A run was carried out under the conditions of Example 22 except the reaction temperature was 200° C. The EBD conversion was 94% and the selectivity to 3-methyl-1,3-pentadiene was 16%. Mostly oligomers were detected.

EXAMPLE 24

Control

A run was carried out under the conditions of Example 8 except the catalyst was 1.0 P/B with 1% graphite by weight. The 3-methyl-1,3-pentadiene conversion was 60% and the EBD selectivity was 6%. Mostly oligomers were detected. This control demonstrates that the use of graphite is not beneficial unless the P/B ratio is less than 1.0.

EXAMPLE 25

Control

A run was carried out under the conditions of Example 24 except the reaction temperature was 350° C. The 3-methyl-1,3-pentadiene conversion was 52% and the EBD selectivity was 11%. Mostly oligomers were detected.

EXAMPLE 26

Control

A run was carried out under the conditions of Example 1 except the catalyst was a 0.6 P/B with 1% graphite by weight. The EBD conversion was 57% and the 3-methyl-1,3-pentadiene selectivity was 14%. Mostly lights and oligomers were detected. This control demonstrates that the use of graphite is not beneficial unless the P/B ratio is greater than 0.6.

EXAMPLE 27

Control

A run was carried out under the conditions of Example 26 except the reaction temperature was 275° C. The EBD conversion was 78% and the selectivity to 3-methyl-1,3-pentadiene was 48%. Mostly lights and oligomers were detected.

EXAMPLE 28

Control

A run was carried out under the conditions of Example 8 except the catalyst was a 0.6 P/B with 1% graphite by weight. The 3-methyl-1,3-pentadiene conversion was 17% and the EBD selectivity was 20%. Mostly lights and oligomers were detected. This control demonstrates that the use of graphite is not beneficial unless the P/B ratio is greater than 0.6.

EXAMPLE 29

Control

A run was carried out under the conditions of Example 28 except the reaction temperature was 350° C. The 3-methyl-1,3-pentadiene conversion was 27% and the EBD selectivity was 23%. Mostly lights and oligomers were detected.

From results of the control experiments, it is evident that a boron phosphate catalyst with a P/B ratio of 1.0 or greater or 0.6 or less is inferior to the catalyst described and claimed herein.

Industrial Applicability

As demand for new and different polymers increase and the supply of novel monomers becomes increasingly difficult, there will be a need for alternative methods of obtaining polymerizable monomeric materials. The instant invention provides a process that utilizes a catalyst that overcomes the limitations previously found in the isomerization of branched dienes. Thus, the industry now has a catalyst and process that is superior to those catalysts and isomerization processes previously used. It is the unexpected and unobvious use of a boron phosphate catalyst as described and claimed herein that provides an advancement in the art of monomer production.

Although the present invention has been described herein with reference to preferred typical embodiments thereof, it will be apparent to those skilled in the art that there may be modifications made in the process hereof.

What is claimed is:

1. In the process for the isomerization of a branched diene which comprises passing the branched diene in the vapor phase over a boron phosphate catalyst, the improvement comprising a catalyst which has an initial molar ratio of P/B of less than 1.0 but more than 0.6.

2. A process for the conversion of 2-ethyl-1,3-butadiene to 3-methyl-1,3-pentadiene which comprises contacting the 2-ethyl-1,3-butadiene in the vapor phase at a temperature of from 100° to 200° C. with a boron phosphate catalyst, said catalyst is characterized in that the initial molar ratio of phosphorus (P) to boron (B) (P/B) is less than 1.0 but greater than 0.6.

3. A process for the conversion of 2-ethyl-1,3-butadiene to 3-methyl-1,3-pentadiene as specified in claim 2 wherein the boron phosphate catalyst is in physical admixture with from 0.1 to 10 weight percent graphite.

4. A process for the conversion of 3-methyl-1,3-pentadiene to 2-ethyl-1,3-butadiene which comprises contacting the 3-methyl-1,3-pentadiene in the vapor phase at a temperature from 250° to 450° C. with a boron phosphate catalyst, said catalyst is characterized in that the initial molar ratio of phosphorus (P) to boron (B) (P/B) is less than 1.0 but greater than 0.6.

5. A process for the conversion of 3-methyl-1,3-pentadiene to 2-ethyl-1,3-butadiene as specified in claim 4 wherein the boron phosphate catalyst is in physical admixture with from 0.1 to 10 weight percent graphite.

6. In the process for the conversion of 3-methyl-1,3-pentadiene to 2-ethyl-1,3-butadiene which comprises contacting the 3-methyl-1,3-pentadiene in the vapor phase at a temperature from 250° to 450° C. at a LHVS of 1.0 to 20 with a boron phosphate catalyst, the improvement characterized in that the boron phosphate containing catalyst is prepared by (1) combining phosphoric acid and boric acid and/or trialkyl borate wherein the alkyl group is from 1 to 6 carbon atoms; (2) at such molar ratios that the molar ratio of P/B is less than 1 but greater than 0.6 thus forming boron phosphate; (3) admixing the resulting boron phosphate with from 0.1 to 10 weight percent graphite based on total weight of the resultant boron phosphate; (4) calcining the resultant boron phosphate, graphite admixture in air at a temperature from 250° to 650° C. for 1 to 6 hours; and (5) steaming the calcined boron phosphate, graphite mixture at 200° to 300° C. for ½ to 10 hours.

7. In the process for the conversion of 2-ethyl-1,3-butadiene to 3-methyl-1,3-pentadiene which comprises contacting the 2-ethyl-1,3-butadiene in the vapor phase at a temperature from 100° to 200° C. at a LHSV of 1.0 to 20 with a boron phosphae catalyst, the improvement characterized in that the boron phosphate containing catalyst is prepared by (1) combining phosphoric acid and boric acid and/or trialkyl borate wherein the alkyl group is from 1 to 6 carbon atoms; (2) at such molar ratios that the molar ratio of P/B is less than 1 but greater than 0.6, thus forming boron phosphate; (3) admixing the resulting boron phosphate with from 0.1 to 10 weight percent graphite based on total weight of the resultant boron phosphate; (4) calcining the resultant boron phosphate, graphite admixture in air at a temperature from 250° to 650° C. for 1to 6 hours; and (5) steaming the calcined boron phosphate, graphite mixture at 200° to 300° C. for ½ to 10 hours.

8. A process according to claim 1 wherein the branched diene is selected from the group comprising 2-ethyl-1,3-butadiene: 3-methyl-1,3-pentadiene; 2-methyl-1,3-pentadiene; and 4-methyl-1,3-pentadiene.

9. A process according to claim 1 wherein the catalyst has an initial molar ratio of P/B of less than 0.9 but more than 0.7.

10. A process according to claim 1 wherein the catalyst is in physical admixture with from 0.5 to 5% graphite by weight.

11. A process according to claim 2 wherein the temperature is from 150° to 200° C.

12. A process according to claim 4 wherein the temperature is from 275° to 400° C., the P/B ratio is from 0.9 to 0.7.

13. A process according to claim 6 wherein the LHSV is from 1.5 to 3.5.

14. A process according to claim 7 wherein the LHSV is from 1.5 to 3.5.

* * * * *